(12) United States Patent
Hashimoto

(10) Patent No.: US 6,860,853 B2
(45) Date of Patent: Mar. 1, 2005

(54) ULTRASONIC IMAGING APPARATUS

(75) Inventor: Hiroshi Hashimoto, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 51 days.

(21) Appl. No.: 10/419,568

(22) Filed: Apr. 21, 2003

(65) Prior Publication Data
US 2003/0204139 A1 Oct. 30, 2003

(30) Foreign Application Priority Data
Apr. 26, 2002 (JP) ........................................ 2002-125813

(51) Int. Cl.⁷ ................................................ A61B 8/14
(52) U.S. Cl. ..................................... 600/446; 128/916
(58) Field of Search ................................ 600/407–472; 73/595–633; 367/7, 11, 130, 138; 128/916

(56) References Cited

U.S. PATENT DOCUMENTS

| | | | |
|---|---|---|---|
| 4,361,044 A | 11/1982 | Kupperman et al. | |
| 5,224,467 A | 7/1993 | Oku | |
| 5,701,900 A | 12/1997 | Shehada et al. | |
| 6,405,072 B1 | * 6/2002 | Cosman | ...................... 600/426 |

* cited by examiner

Primary Examiner—Ali Imam
(74) Attorney, Agent, or Firm—Carl B. Horton, Esq.; Armstrong Teasdale LLP

(57) ABSTRACT

For the purpose of allowing easy perception of the imaging direction of an image produced by post-processing, the present apparatus comprises: data acquiring means for acquiring three-dimensional image data on a subject to be imaged based on ultrasound using an ultrasonic transceiver; specifying means for specifying a simulative imaging direction based on spatial information with respect to a hand instrument that is manually operated; and image producing means for producing an image corresponding to an image captured in the simulative imaging direction based on the three-dimensional image data.

16 Claims, 20 Drawing Sheets

Actual scan region

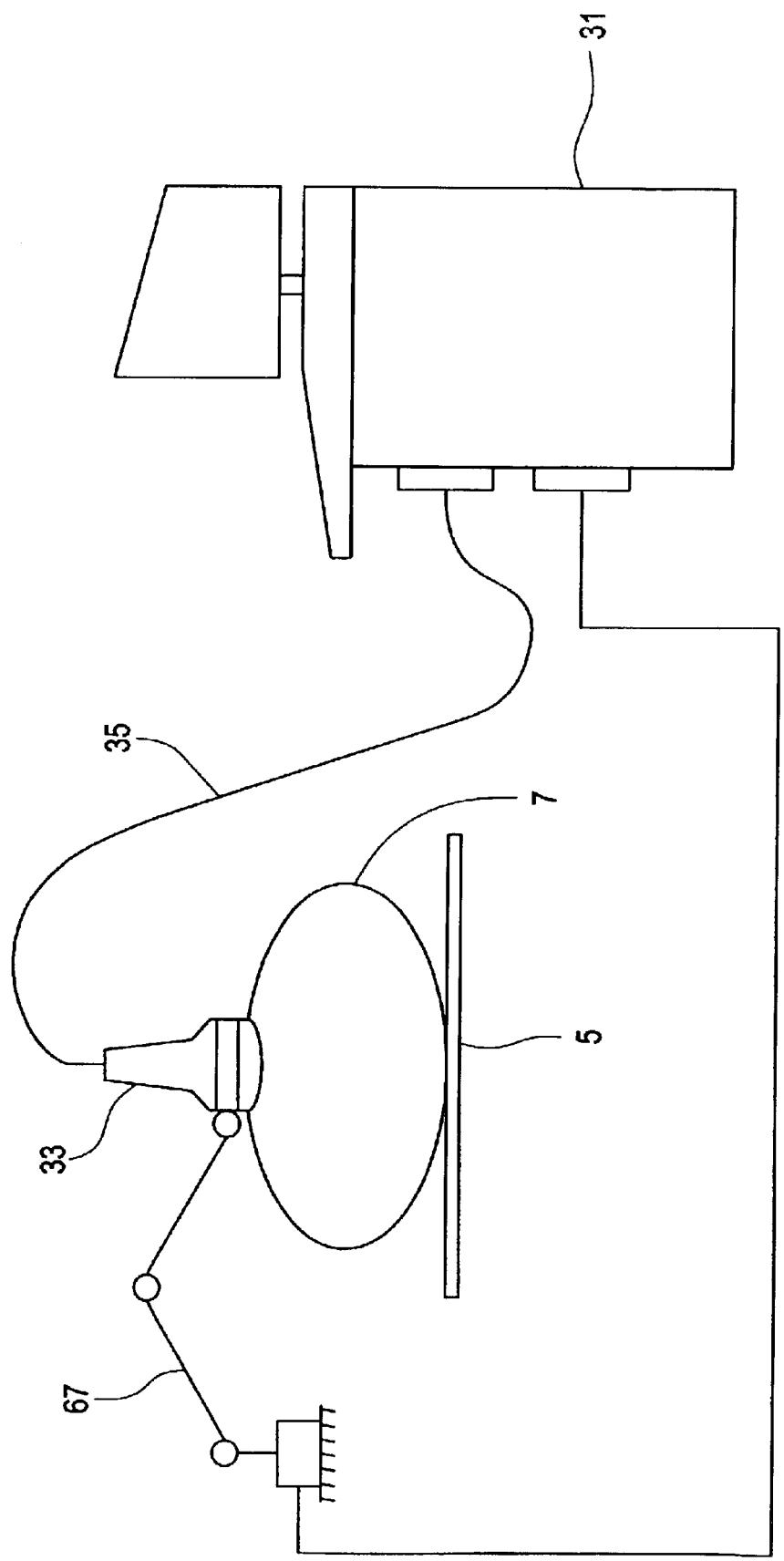

ULTRASONIC IMAGING APPARATUS

CROSS REFERENCE TO RELATED APPLICATIONS

This application claims the benefit of Japanese Application No. 2002-125813 filed Apr. 26, 2002.

BACKGROUND OF THE INVENTION

The present invention relates to an ultrasonic imaging apparatus, and more particularly to an ultrasonic imaging apparatus for capturing a three-dimensional image.

An ultrasonic imaging apparatus scans the interior of a subject to be imaged by an ultrasonic beam, receives an echo, generates image data corresponding to the intensity of the echo, and produces what is generally called a B-mode image based on the image data. When a three-dimensional image is to be captured, the scan by the ultrasonic beam is conducted in a three-dimensional manner to acquire three-dimensional image data. The scan by the ultrasonic beam is sometimes referred to as an acoustic line scan.

By applying suitable processing to the three-dimensional image data after the image capture, a three-dimensional image as viewed in an arbitrary direction is produced. Alternatively, a tomographic image of an arbitrary cross section may be produced. Such processing is sometimes referred to as post-processing.

An image produced by the post-processing corresponds to an image that is captured in a direction different from an actual imaging direction. By additionally using such an image, diagnosis can be made more efficiently.

When an image corresponding to one captured in a direction different from an actual imaging direction is produced by the post-processing, a diagnostician must perceive the spatial relationship between the imaging direction and the subject. However, since all images are displayed in the same orientation as viewed by the diagnostician, it is difficult to perceive the spatial relationship from the displayed image.

SUMMARY OF THE INVENTION

It is therefore an object of the present invention is to provide an ultrasonic imaging apparatus that allows easy perception of the imaging direction of an image produced by post-processing.

The present invention for solving the aforementioned problem is an ultrasonic imaging apparatus characterized in comprising: data acquiring means for acquiring three-dimensional image data on a subject to be imaged based on ultrasound using an ultrasonic transceiver; specifying means for specifying a simulative imaging direction based on spatial information with respect to a hand instrument that is manually operated; and image producing means for producing an image corresponding to an image captured in said simulative imaging direction based on said three-dimensional image data.

According to the present invention, a simulative imaging direction is specified by specifying means based on positional information with respect to a hand instrument that is manually operated, and an image corresponding to an image captured in the simulative imaging direction is produced by the image producing means based on the three-dimensional image data, so that an user can easily perceive the imaging direction from the spatial location and orientation of the hand instrument that the user himself is operating.

Preferably, the specifying means has detecting means for detecting a three-dimensional location and attitude of the hand instrument, so that the specification of the simulative imaging direction based on the spatial information is properly achieved.

Detecting means using magnetism to conduct the detection is preferable in that three-dimensional coordinates are obtained based on the magnetic field strength.

A hand instrument having a magnetic sensor is preferable in that the magnetic field strength is detected.

Detecting means using light to conduct the detection is preferable in that three-dimensional coordinates are optically obtained.

A hand instrument having a light emitter is preferable in that the optical detection is facilitated.

Detecting means using acceleration to conduct the detection is preferable in that three-dimensional coordinates are obtained based on a law of motion.

A hand instrument having an acceleration sensor is preferable in that the acceleration of the hand instrument is detected.

Detecting means conducting the detection based on angles of joints in an articulated arm linked to the hand instrument is preferable in that three-dimensional coordinates are obtained by mechanical means.

A detecting means in which a reference position for detecting the three-dimensional location and attitude of the hand instrument can be set by a user of the hand instrument is preferable in that specification of the simulative imaging direction is facilitated.

A hand instrument doubling as the ultrasonic transceiver is preferable in that a feeling of incompatibility is prevented.

A hand instrument that is a dedicated direction indicator is preferable in that discrimination from actual imaging is facilitated.

Data acquiring means having scanning means for electronically conducting a three-dimensional acoustic line scan is preferable in that the three-dimensional image data is acquired at a high speed.

A data acquiring means having scanning means for conducting the three-dimensional acoustic line scan by a combination of an electronic scan and a mechanical scan is preferable in that the three-dimensional image data is acquired with good spatial resolution.

An image that is a three-dimensional image is preferable in that a three-dimensional structure is represented.

An image that is a tomographic image is preferable in that a two-dimensional structure is represented.

Therefore, the present invention provides an ultrasonic imaging apparatus that allows easy perception of the imaging direction of an image produced by post-processing.

Further objects and advantages of the present invention will be apparent from the following description of the preferred embodiments of the invention as illustrated in the accompanying drawings.

BRIEF DESCRIPTION OF THE DRAWINGS

FIG. 20 schematically shows a configuration of the apparatus in accordance with one embodiment of the present invention.

DETAILED DESCRIPTION OF THE INVENTION

Figure 1:
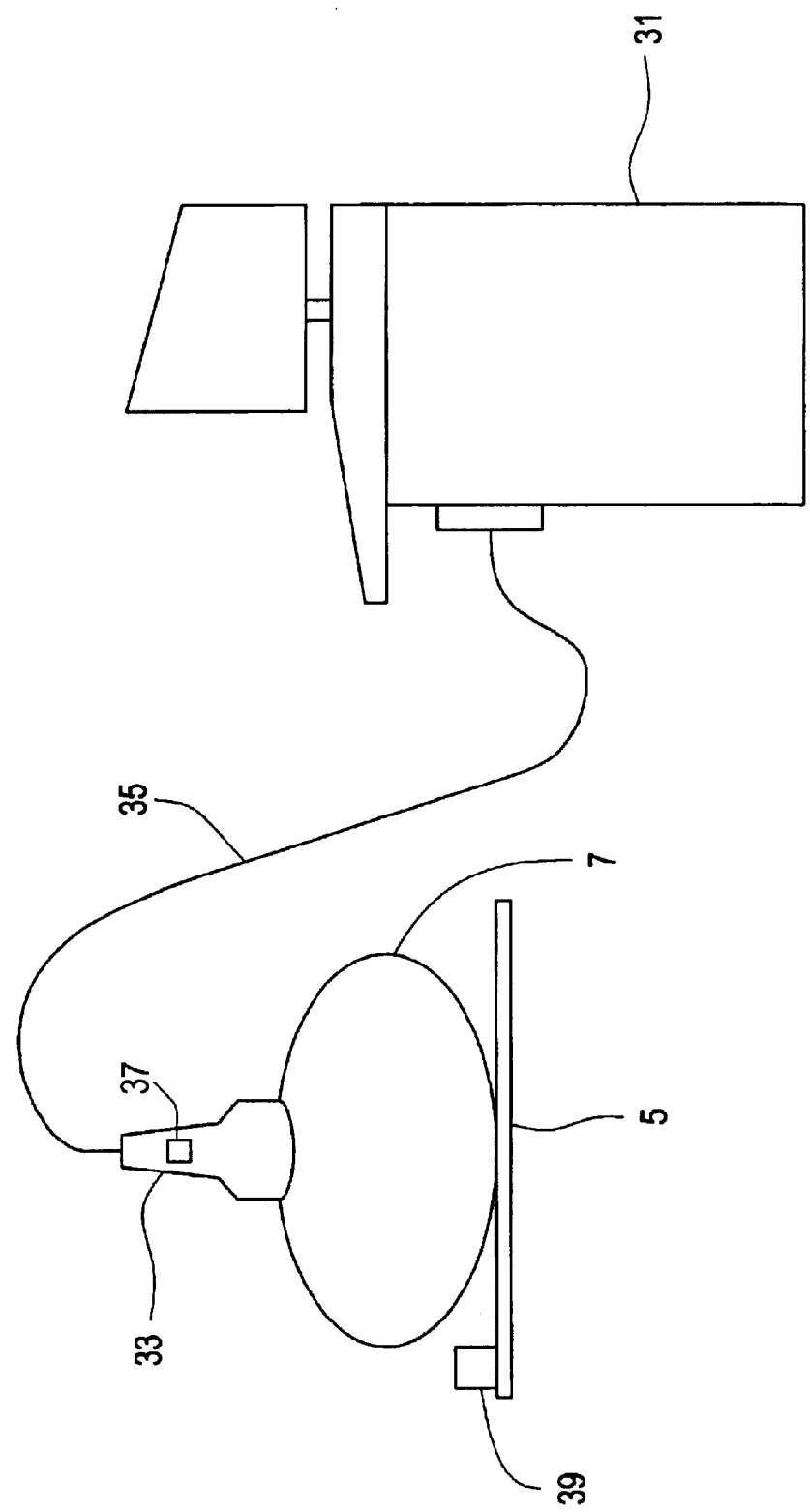
FIG. 1 schematically shows a configuration of an apparatus in accordance with one embodiment of the present invention.

Embodiments of the present invention will be hereinbelow described in detail with reference to the accompanying drawings. It should be noted that the present invention is not limited to the embodiments. FIG. 1 shows a schematic diagram of an ultrasonic imaging apparatus. The apparatus is an embodiment of the present invention. The configuration of the apparatus represents an embodiment of the apparatus in accordance with the present invention.

As shown in FIG. 1, the apparatus comprises an imaging section main body 31 and an ultrasonic probe 33. The ultrasonic probe 33 is connected to the imaging section main body 31 via a cable 35. The ultrasonic probe 33 is used by a user applying it against the surface of a subject 7. The subject 7 is placed on a support plate 5.

The ultrasonic probe 33 is driven by a driving signal supplied by the imaging section main body 31 via the cable 35 to scan the interior of the subject 7 by an ultrasonic beam, and it receives an echo of the ultrasound and inputs a signal of the received echo to the imaging section main body 31 via the cable 35. The imaging section main body 31 produces an image based on the echo received signal, and displays the image on a display.

The ultrasonic probe 33 comprises a position sensor 37. The position sensor 37 detects the three-dimensional location and attitude of the ultrasonic probe 33. The three-dimensional location and attitude are detected based on, for example, a magnetic field generated by a magnetic field generator 39. The position sensor 37 is made using a magnetic sensor. The magnetic field generator 39 is disposed at an appropriate position, for example, on the support plate 5.

Since the magnetic field generated by the magnetic field generator 39 varies in strength and direction for each point in the three-dimensional space, the three-dimensional location and attitude of the ultrasonic probe 33 can be detected by detecting the varying magnetic field by the position sensor 37. The position sensor 37 is an embodiment of the detecting means of the present invention. The detected signal is input to the imaging section main body 31 via the cable 35.

Figure 2:
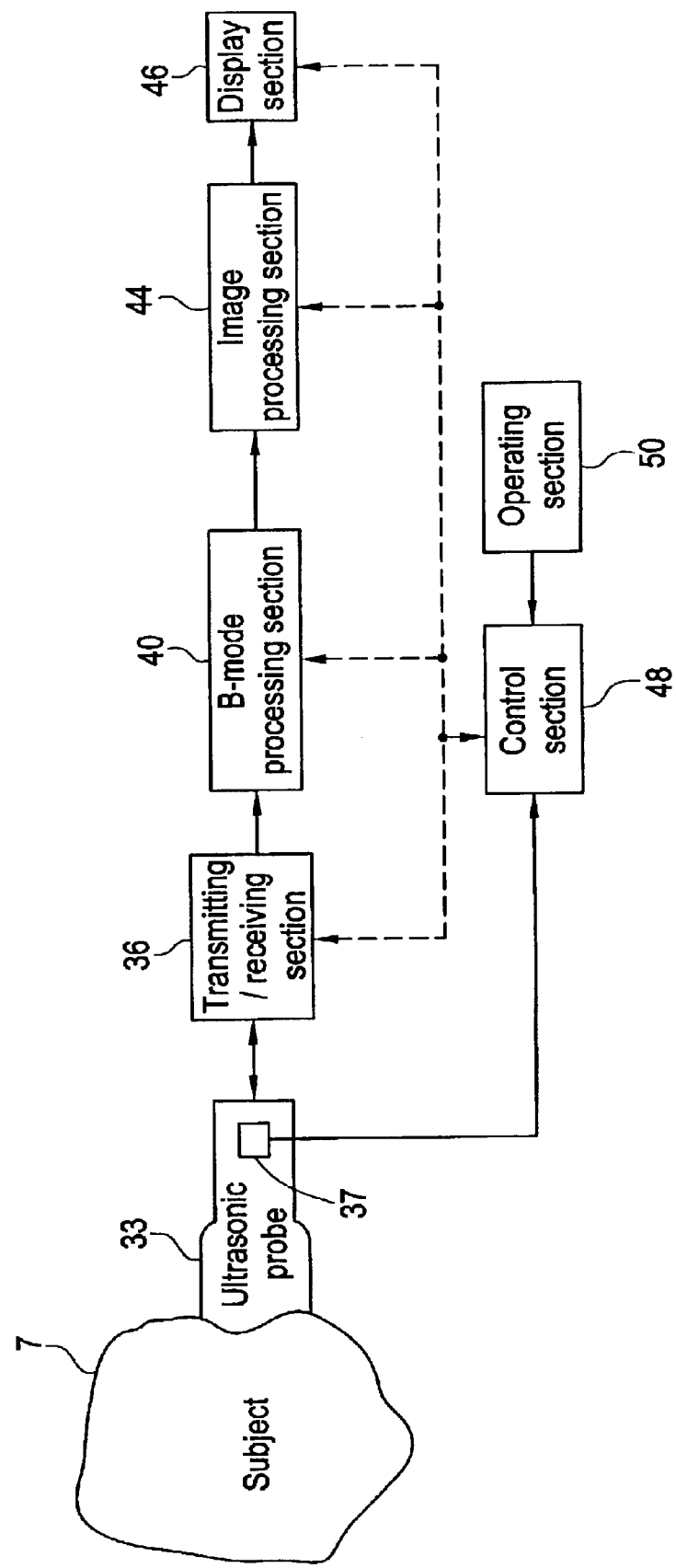
FIG. 2 is a block diagram of the apparatus in accordance with one embodiment of the present invention.

FIG. 2 shows a block diagram of the present apparatus. The ultrasonic probe 33 is connected to a transmitting/receiving section 36. The transmitting/receiving section 36 supplies a driving signal to the ultrasonic probe 33 to transmit ultrasound. The transmitting/receiving section 36 also receives an echo signal received by the ultrasonic probe 33.

Figure 3:
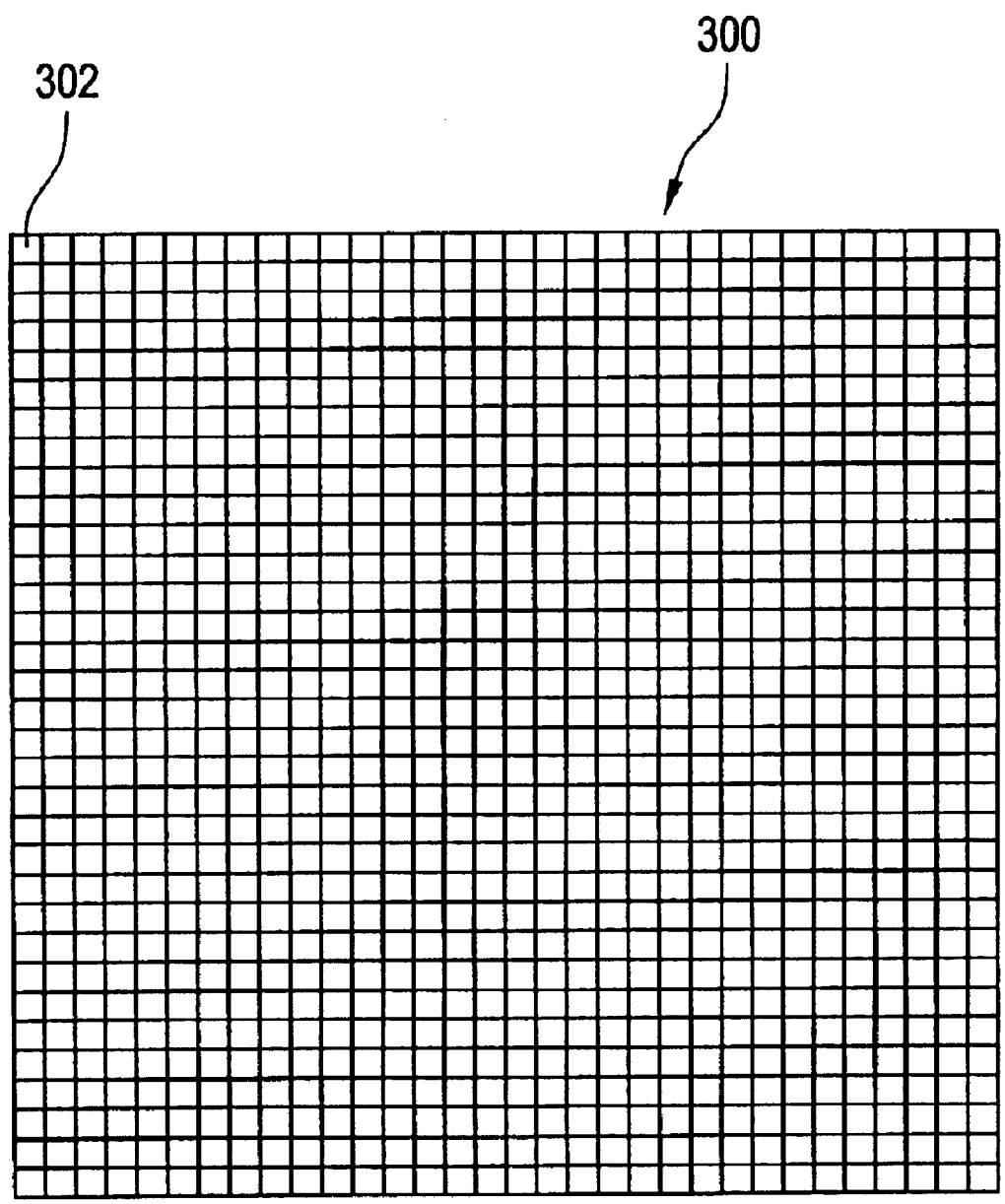
FIG. 3 is a schematic diagram of an ultrasonic transducer array.

The ultrasonic probe 33 has an ultrasonic transducer array 300 as exemplarily shown in FIG. 3. The ultrasonic transducer array 300 is a two-dimensional array, and is comprised of 1,024 ultrasonic vibrators 302 forming a 32×32 square matrix, for example. However, the two-dimensional array is not limited to the square matrix, and it may be an anisotropic matrix of 32×16, for example. The ultrasonic vibrators 302 are made of a piezoelectric material such as PZT (lead zirconate titanate [Pb—Zr—Ti]) ceramic. The ultrasonic probe 33 is an embodiment of the ultrasonic transceiver of the present invention.

Figure 4:
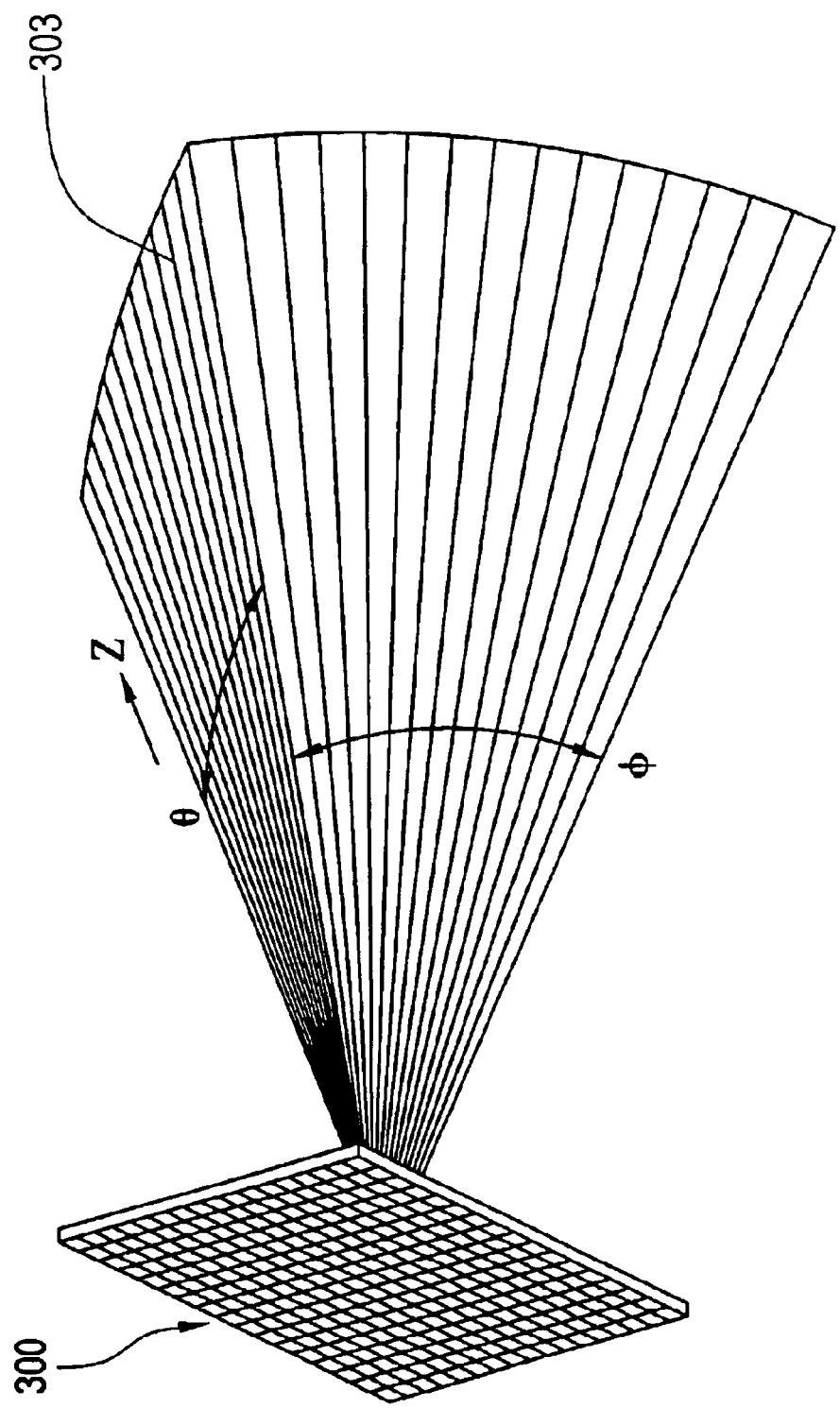
FIG. 4 is a conceptual diagram of an acoustic line scan.

The transmitting/receiving section 36 conducts a scan as exemplarily shown in FIG. 4. Specifically, it conducts a three-dimensional scan by scanning an imaging range having a cone shape with its apex at the center of the transducer array 300 by an ultrasonic beam 303 (acoustic line) in a direction of an angle $\theta$ and in a direction of an angle $\phi$. The direction of the length of the ultrasonic beam 303 is defined as a z-direction. The $\theta$-direction and $\phi$-direction are perpendicular to each other.

Such a three-dimensional scan is sometimes referred to as a pyramidal scan. The pyramidal scan is conducted by an operation of an electronic circuit constituting the transmitting/receiving section 36. Such a scan is sometimes referred to as an electronic scan. The electronic scan can achieve the acoustic line scan at a high speed. A portion including the ultrasonic probe 33 and the transmitting/receiving section 36 is an embodiment of the scanning means of the present invention.

The transmitting/receiving section 36 is connected to a B-mode processing section 40. The echo received signal for each acoustic line output from the transmitting/receiving section 36 is input to the B-mode processing section 40. The B-mode processing section 40 generates B-mode image data. Specifically, the B-mode processing section 40 logarithmically amplifies the echo received signal, detects its envelope to acquire a signal indicating the intensity of the echo at each reflection point on an acoustic line, and generates the B-mode image data using the amplitude of the signal at each instant as the brightness. A portion including the ultrasonic probe 33, transmitting/receiving section 36 and B-mode processing section 40 is an embodiment of the data acquiring means of the present invention.

The B-mode processing section 40 is connected to an image processing section 44. The image processing section 44 produces a B-mode image based on data supplied from the B-mode processing section 40.

Figure 5:
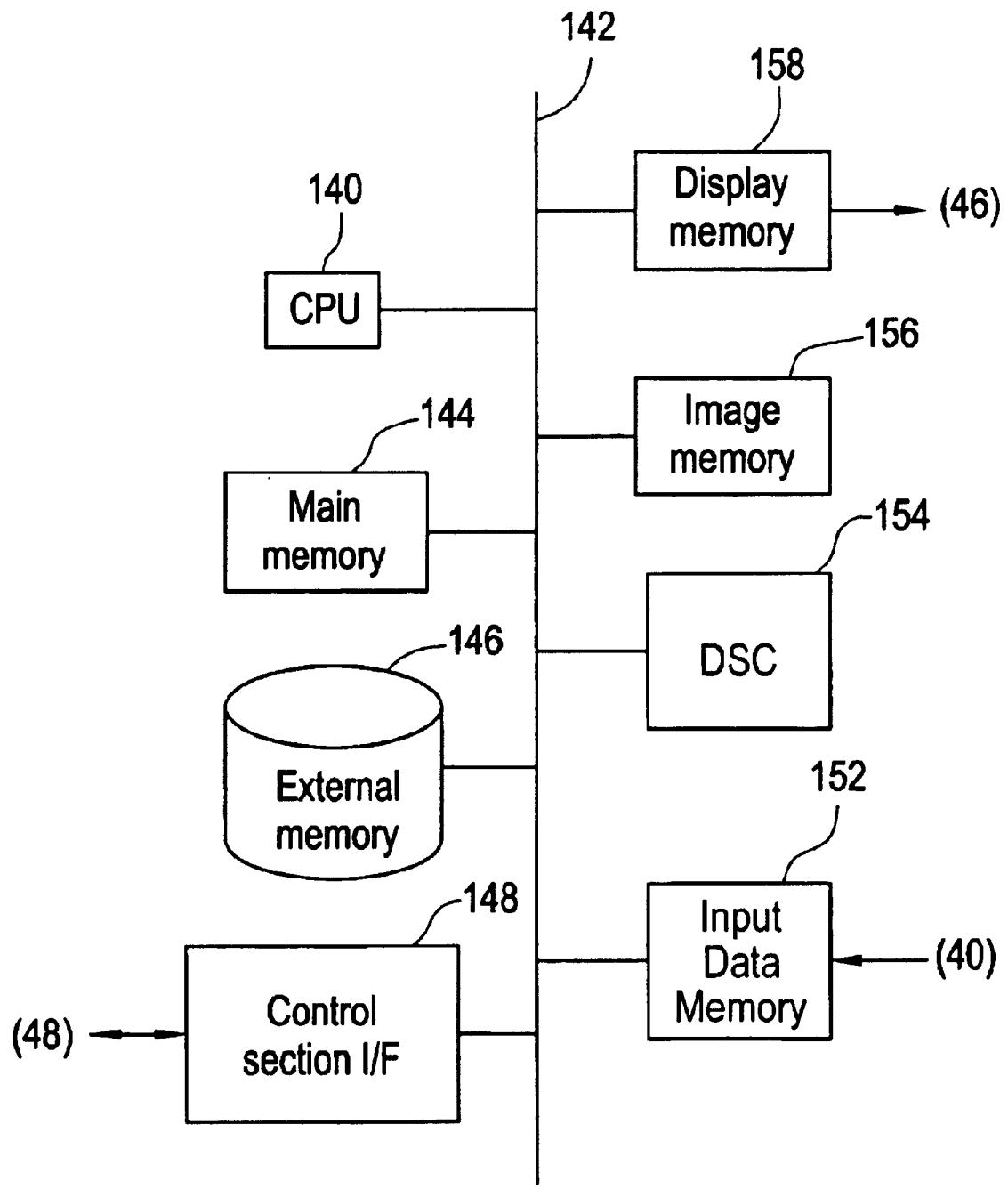
FIG. 5 is a block diagram of an image processing section.

The image processing section 44 comprises a central processing unit (CPU) 140, as shown in FIG. 5. The CPU 140 is connected with a main memory 144, an external memory 146, a control section interface 148, an input data memory 152, a digital scan converter (DSC) 154, an image memory 156 and a display memory 158 via a bus 142.

The external memory 146 stores programs executed by the CPU 140. It also stores several kinds of data for use by the CPU 140 in executing the programs.

The CPU 140 carries out predetermined image processing by loading a program from the external memory 146 into the main memory 144 for execution. The CPU 140 communicates control signals with a control section 48, which will be described later, via the control section interface 148 in the course of the program execution.

The B-mode image data supplied from the B-mode processing section 40 for each acoustic line is stored in the input data memory 152. The data in the input data memory 152 are scan-converted at the DSC 154 and stored in the image memory 156. The data in the image memory 156 are output to a display section 46 via the display memory 158.

The image processing section 44 is connected with the display section 46. The display section 46 is supplied with an image signal from the image processing section 44, and displays an image based on the image signal. The display section 46 comprises a graphic display or the like employing a CRT (cathode ray tube) capable of displaying a color image. A portion including the image processing section 44 and display section 46 is an embodiment of the image producing means of the present invention.

The transmitting/receiving section 36, B-mode processing section 40, image processing section 44 and display section 46 are connected with the control section 48. The control section 48 comprises a computer, for example.

The control section 48 supplies control signals to these sections to control their operation. The control section 48 is supplied with several kinds of notification signals from the controlled sections. The B-mode operation is executed under control of the control section 48.

The control section 48 is also supplied with the detected signal of the position sensor 37. The control section 48 recognizes the three-dimensional location and attitude of the ultrasonic probe 33 based on the detected signal.

The control section 48 is connected with an operating section 50. The operating section 50 is operated by the user, and it inputs appropriate instructions and information to the control section 48. The operating section 50 comprises, for example, a keyboard, pointing device and other operating devices.

Figure 6:
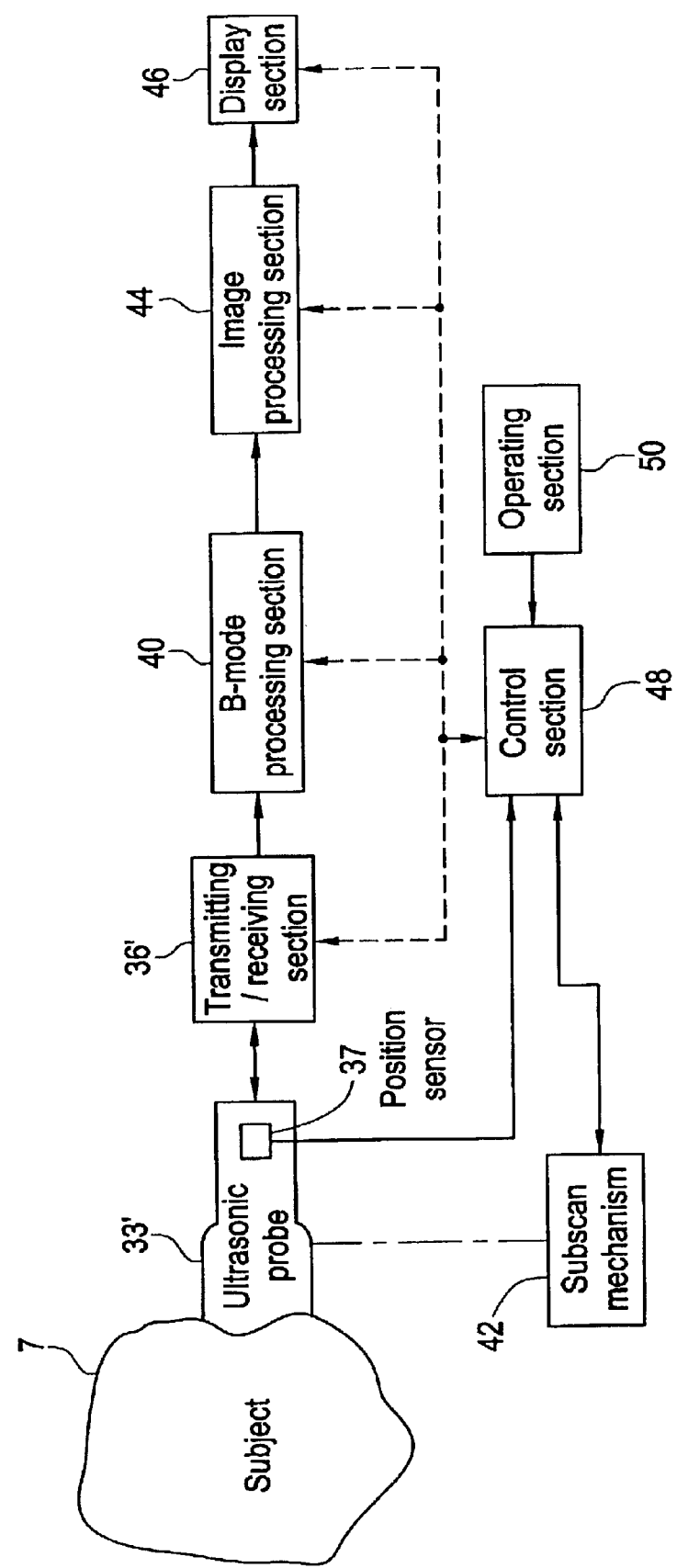
FIG. 6 is a block diagram of the apparatus in accordance with one embodiment of the present invention.
Figure 7:
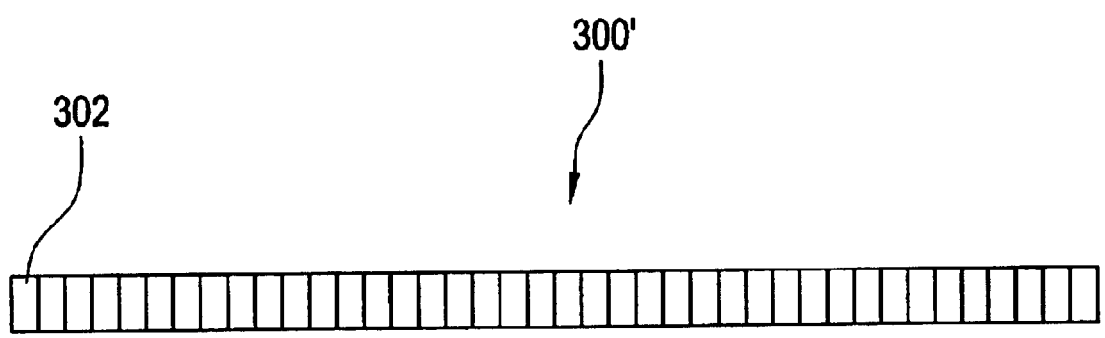
FIG. 7 is a schematic diagram of an ultrasonic transducer array.

FIG. 6 shows another block diagram of the present apparatus. Parts in FIG. 6 that are similar to those shown in FIG. 2 are designated by similar reference numerals and explanation thereof will be omitted. In this apparatus, an ultrasonic probe 33' has an ultrasonic transducer array 300' as exemplarily shown in FIG. 7. The ultrasonic transducer array 300' is a one-dimensional array and is comprised of 128 ultrasonic vibrators 302, for example.

The ultrasonic probe 33' is connected to a transmitting/receiving section 36'. The transmitting/receiving section 36' supplies a driving signal to the ultrasonic probe 33' to transmit ultrasound. The transmitting/receiving section 36' also receives an echo signal received by the ultrasonic probe 33'.

Figure 8:
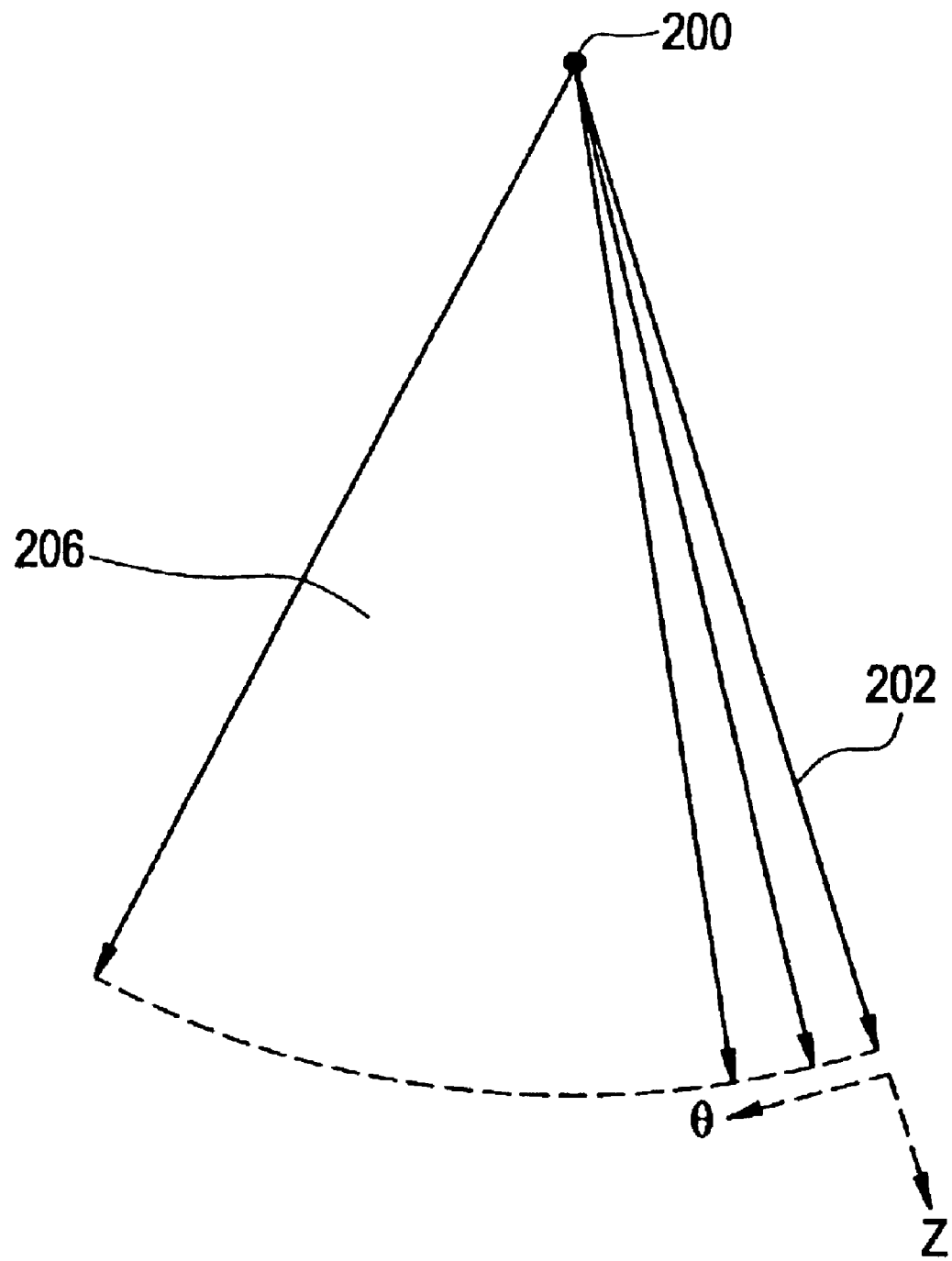
FIG. 8 is a conceptual diagram of an acoustic line scan.

The transmitting/receiving section 36' conducts a scan as exemplarily shown in FIG. 8. Specifically, a fan-shaped two-dimensional region 206 is scanned in the θ-direction by an acoustic line 202 extending from an emission point 200 in the z-direction, and what is generally called a sector scan is carried out. The sector scan is the electronic scan.

Figure 9:
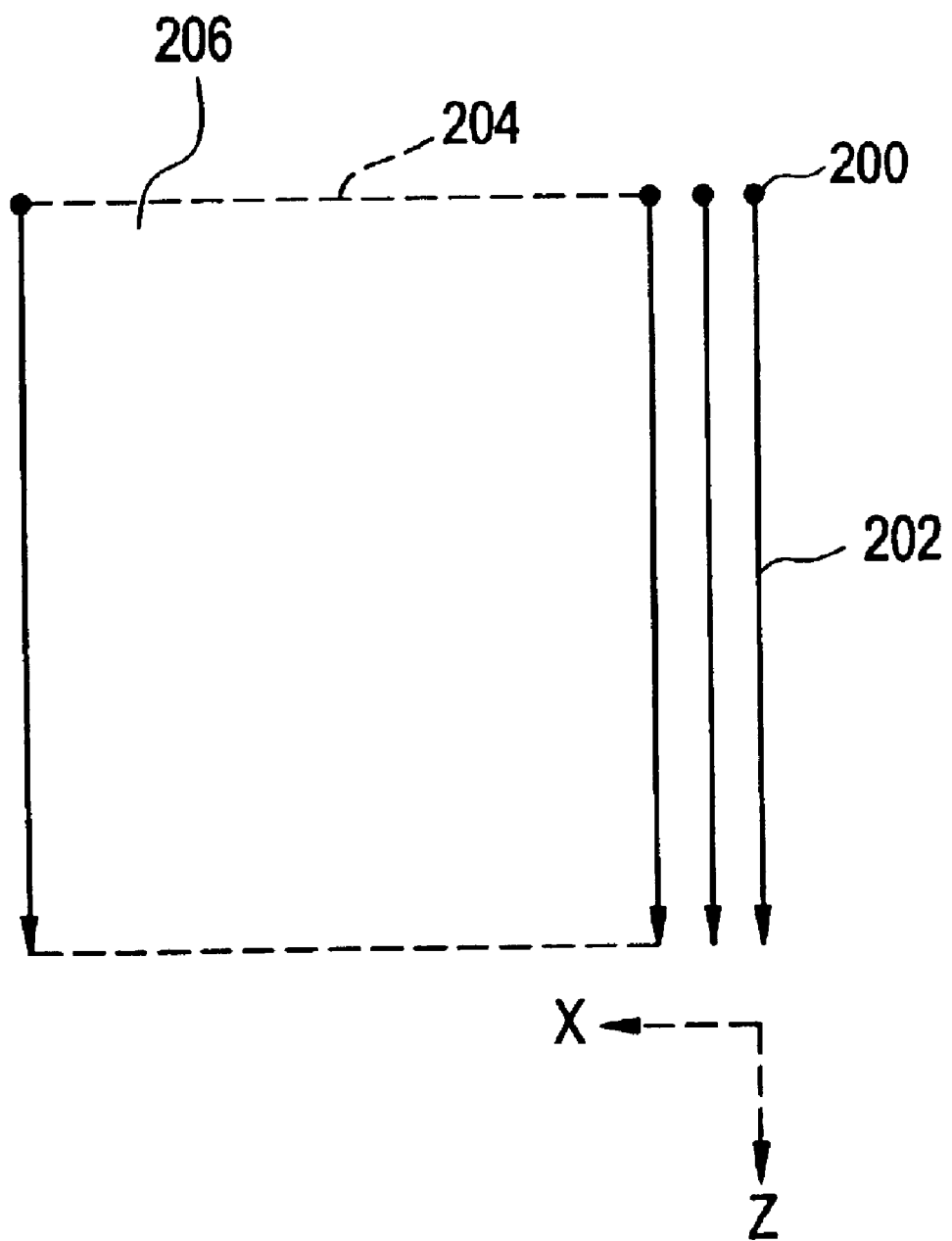
FIG. 9 is a conceptual diagram of an acoustic line scan.

When transmission and reception apertures are formed using part of the ultrasonic transducer array, a scan as exemplarily shown in FIG. 9 can be conducted by sequentially shifting the apertures along the array. Specifically, a rectangular two-dimensional region 206 is scanned in the x-direction by translating an acoustic line 202, which travels from an emission point 200 in the z-direction, along a linear trajectory 204, and what is generally called a linear scan is carried out. The linear scan is also the electronic scan.

Figure 10:
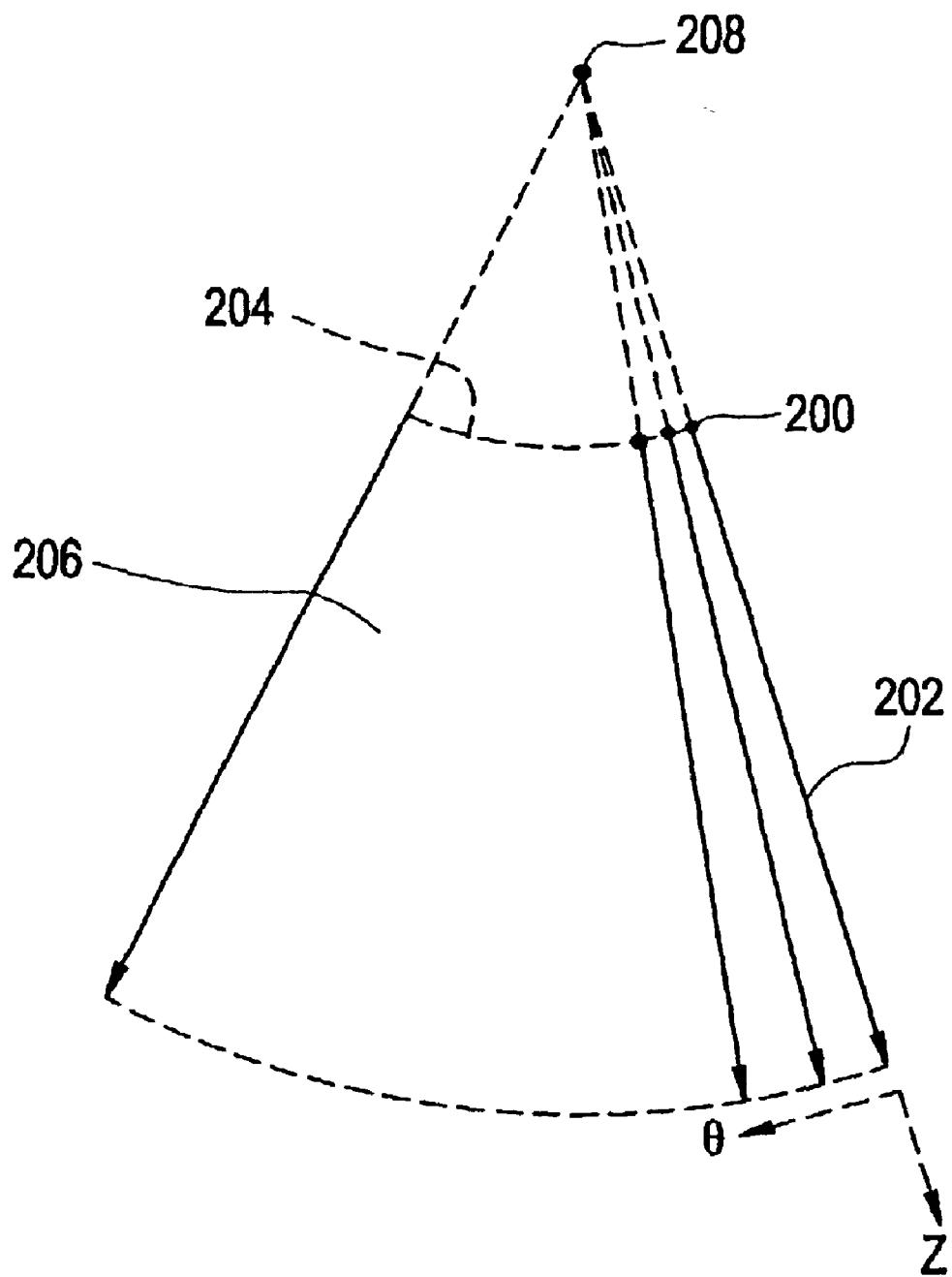
FIG. 10 is a conceptual diagram of an acoustic line scan.

When the ultrasonic transducer array is what is generally called a convex array, which is formed along an arc protruding in the direction of ultrasound transmission, a partial fan-shaped two-dimensional region 206 can be scanned in the θ-direction by an acoustic line scan similar to that for the linear scan with an emission point 200 of an acoustic line 202 moved along an arc-like trajectory 204, as exemplarily shown in FIG. 10, and what is generally called a convex scan is carried out. The convex scan is also the electronic scan.

By conducting such an electronic scan on the two-dimensional region 206 by successively changing the position or inclination of the ultrasonic probe 33', a three-dimensional region can be scanned. The electronic scan will be sometimes referred to as a main scan, and the change of the position or inclination of the ultrasonic probe 33' will be sometimes referred to as a subscan. The subscan is conducted by a subscan mechanism 42 linked to the ultrasonic probe 33'. The subscan may be conducted by a user manual scan.

By conducting the acoustic line scan by a combination of the main scan by the electronic scan and the subscan by the subscan mechanism 42 or manual operation, the spatial resolution of the acoustic line scan is improved.

A portion including the ultrasonic probe 33', transmitting/receiving section 36' and subscan mechanism 42 is an embodiment of the scanning means of the present invention. A portion including the ultrasonic probe 33', subscan mechanism 42, transmitting/receiving section 36' and B-mode processing section 40 is an embodiment of the data acquiring means of the present invention.

Figure 11:
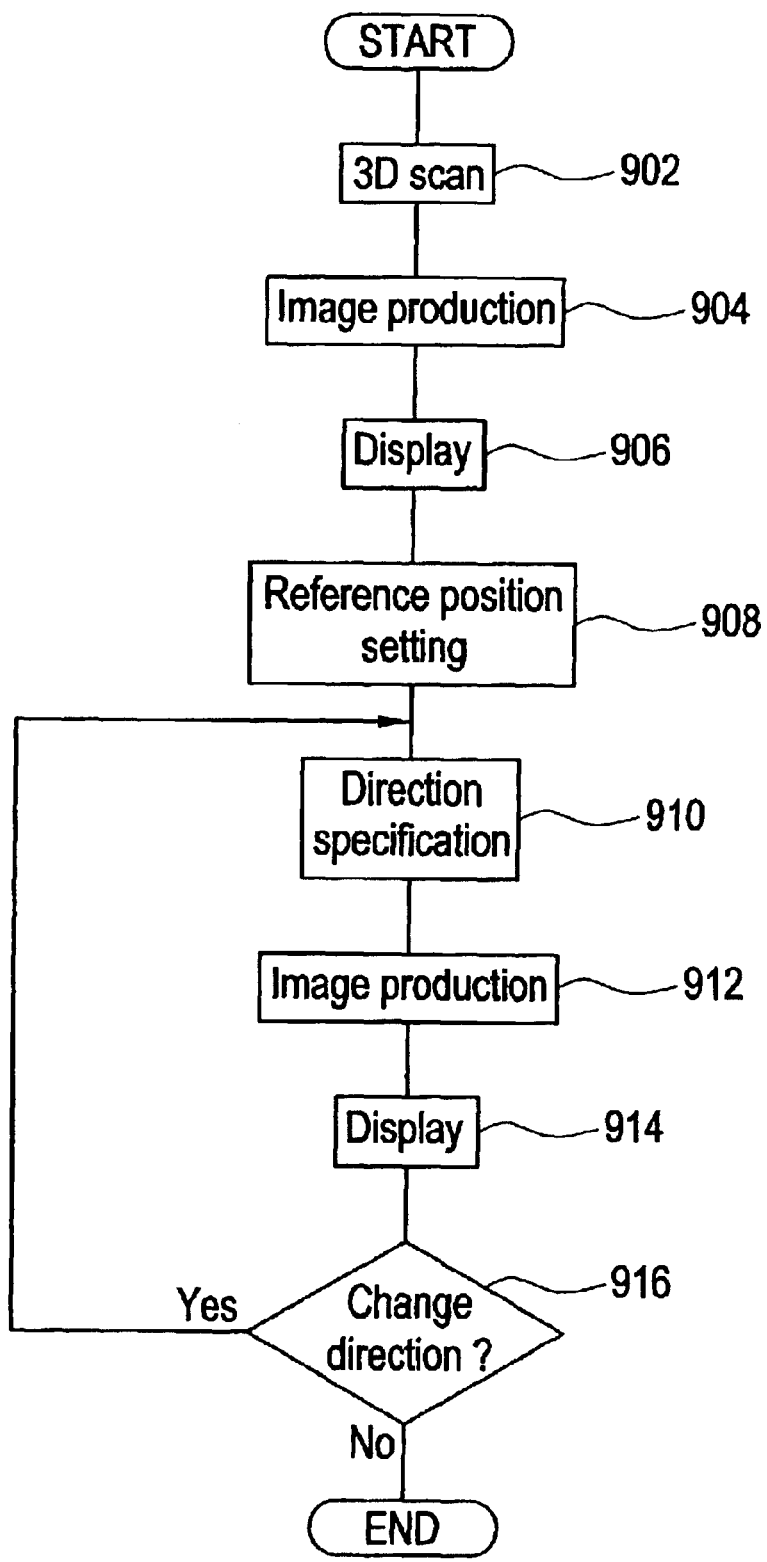
FIG. 11 is a flow chart of an operation of the apparatus in accordance with one embodiment of the present invention.

Now an operation of the present apparatus will be described. FIG. 11 shows a flow chart of the operation of the present apparatus. As shown, a three-dimensional scan is conducted at Step 902. The three-dimensional scan is conducted by the electronic scan or the combination of the electronic main scan and the mechanical subscan. The subscan may be a manual scan.

Figure 12:
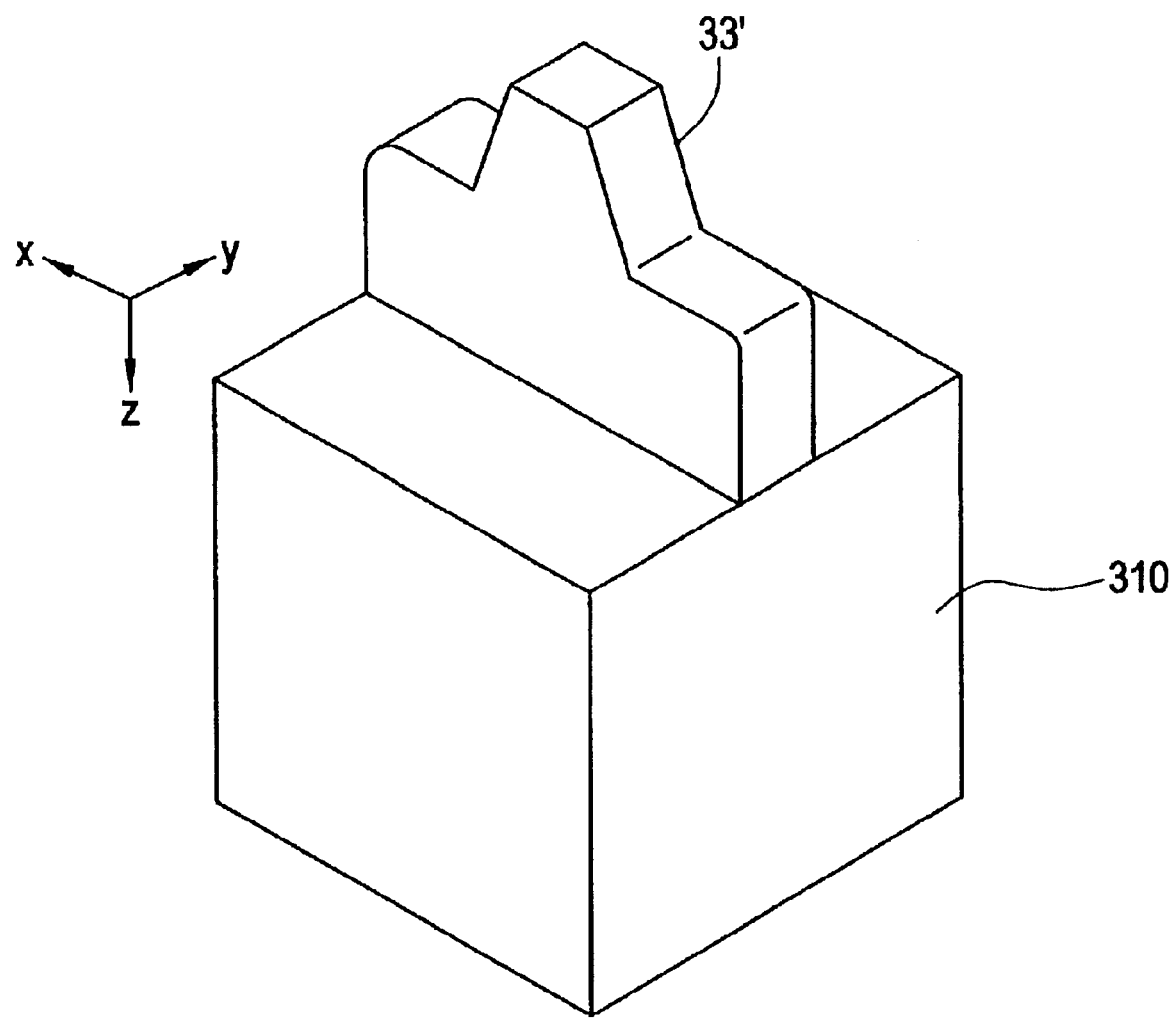
FIG. 12 shows a three-dimensional region.

The three-dimensional scan provides three-dimensional image data. The three-dimensional image data is stored in the image memory 156. The three-dimensional image data is image data representing the internal structure of a three-dimensional region 310 as shown in FIG. 12.

Three mutually orthogonal directions in the three-dimensional region 310 are represented as x, y and z. The x-direction and y-direction correspond to one direction and the other, respectively, in the alignment of the ultrasonic vibrators 302 in the ultrasonic probe 33 (or 33'), for example. The z-direction is a depth direction into the body. It is also an actual imaging direction.

A case in which the ultrasonic probe 33' is employed will be described hereinbelow. The same applies to a case when the ultrasonic probe 33 is employed. In the ultrasonic probe 33', the ultrasonic transducer array is one-dimensional. A direction of the alignment of the ultrasonic vibrators in the face of the ultrasonic transducer array is defined as the x-direction, and a direction perpendicular thereto is defined as the y-direction. A scan in the x-direction is conducted by the main scan. A scan in the y-direction is conducted by the subscan.

Figure 13:
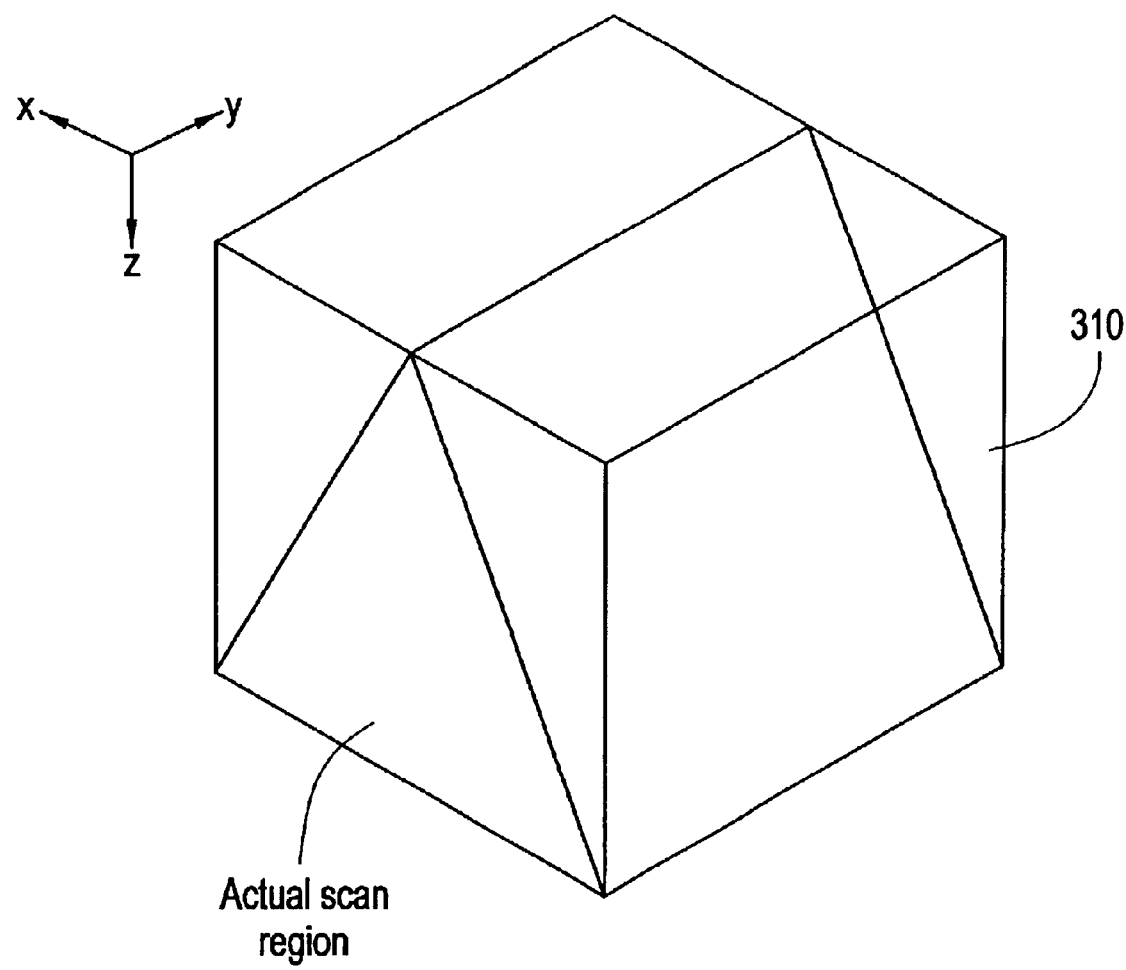
FIG. 13 shows a three-dimensional region.
Figure 14:
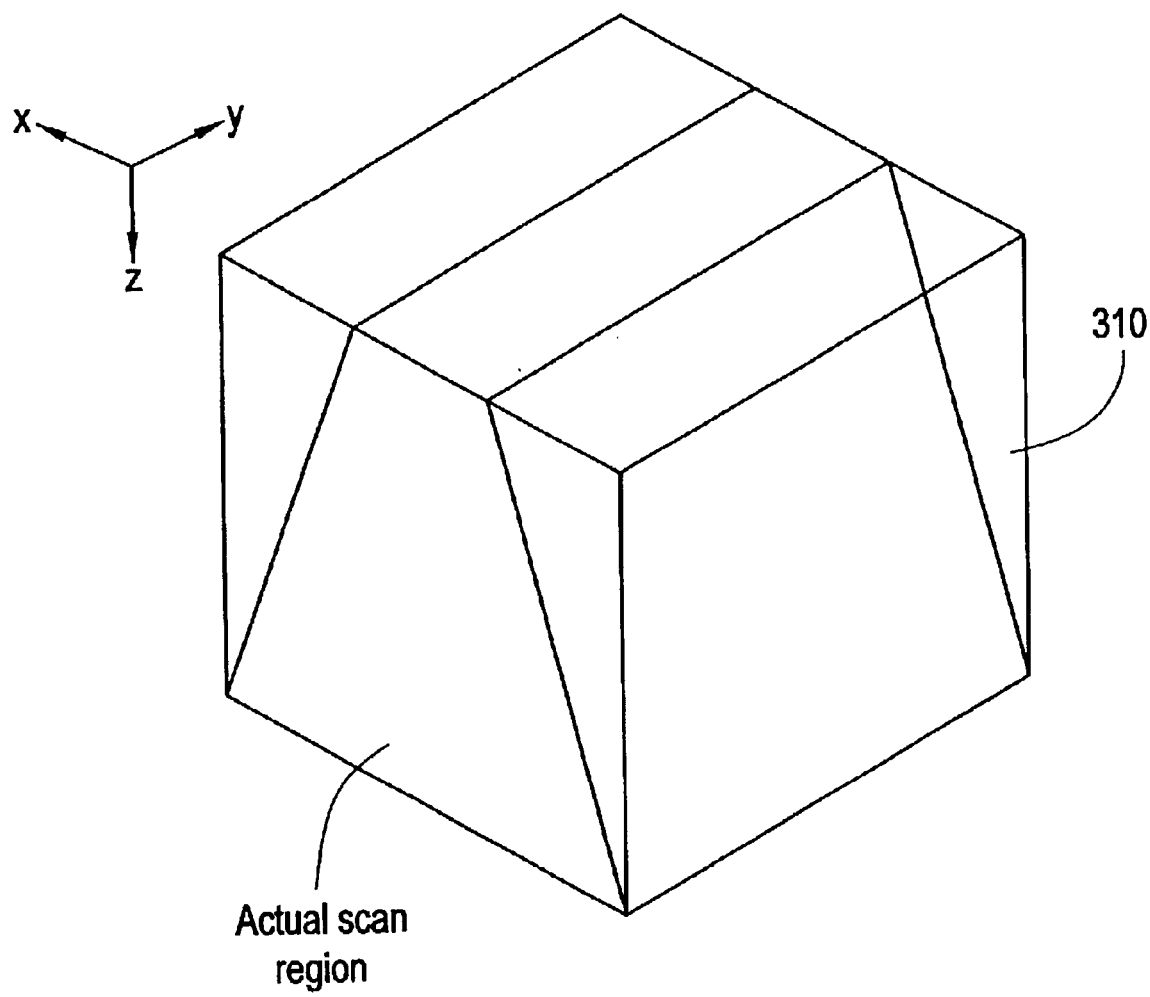
FIG. 14 shows a three-dimensional region.
Figure 15:
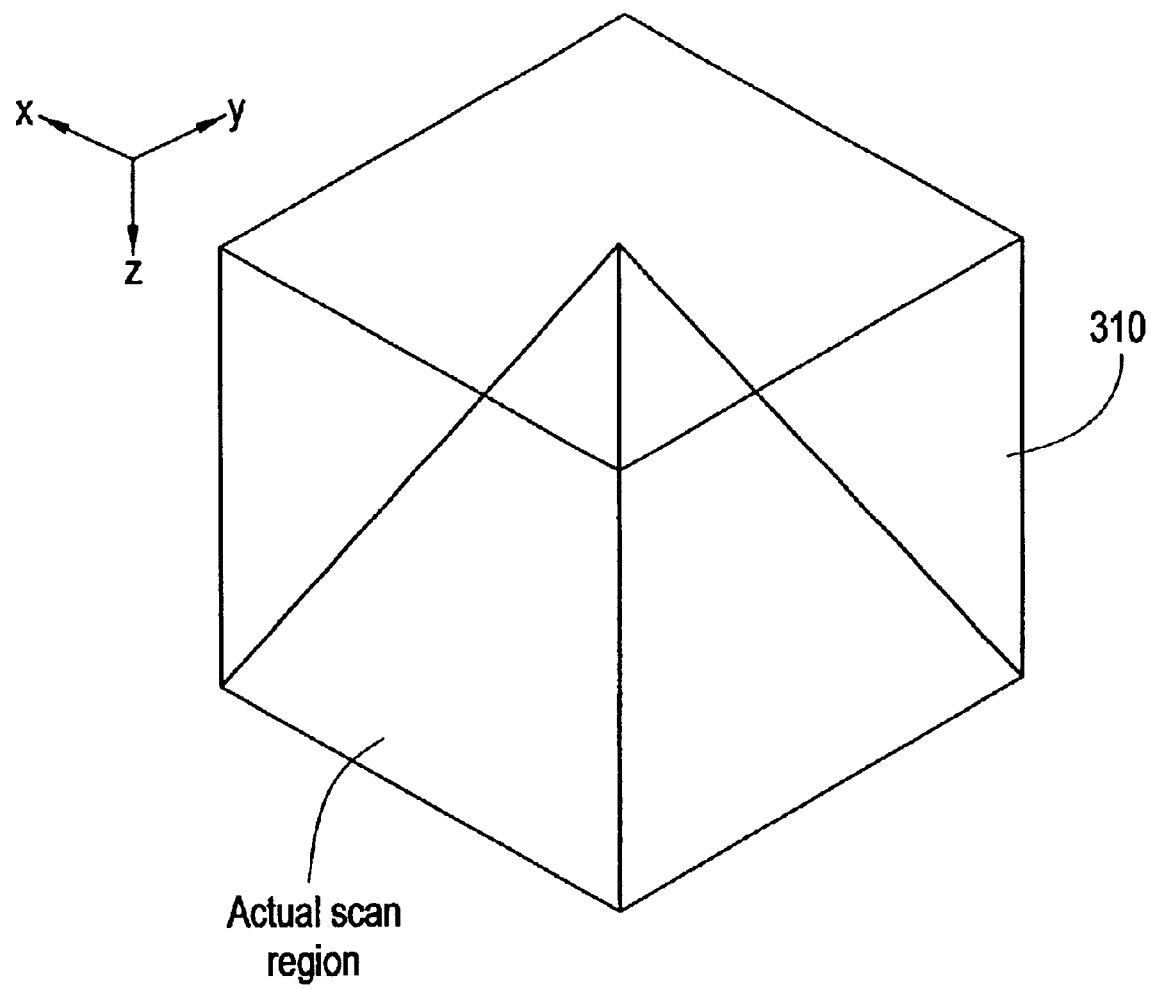
FIG. 15 shows a three-dimensional region.

When the main scan is a linear scan, the whole three-dimensional region is scanned. When the main scan is a sector scan, a triangular prism-shaped region as shown in FIG. 13 is the actual scan region. When the main scan is a convex scan, the actual scan region is trapezoidal prism-shaped as shown in FIG. 14. Additionally, when a pyramidal scan is conducted by the ultrasonic probe 33, the actual scan region is pyramidal as shown in FIG. 15.

Next, image production is conducted at Step 904. The image is produced based on the three-dimensional image data. A three-dimensional image is thus produced. The three-dimensional image is produced as an image of the three-dimensional region 310 as viewed in the y-direction, for example. Such a three-dimensional image is displayed as a visible image at Step 906.

Next, at step 908, reference position setting is conducted. The reference position setting is an operation of defining a spatial reference for direction specification that will be conducted next. The reference position setting is activated by a command from the user.

The user sets a reference position as follows, for example: the user brings the ultrasonic probe 33' away from the subject 7, holding it by a hand, and turns to directly face the present apparatus. Then, the user holds the ultrasonic probe 33' vertically so that the ultrasound emitting face looks downward, and issues the command for the reference position setting to the control section 48 in this condition. The command is issued by, for example, pressing a predetermined button on the operating section 50. In response to the command, the control section 48 stores the three-dimensional location of the ultrasonic probe 33' at that time as the reference position.

Figure 16:
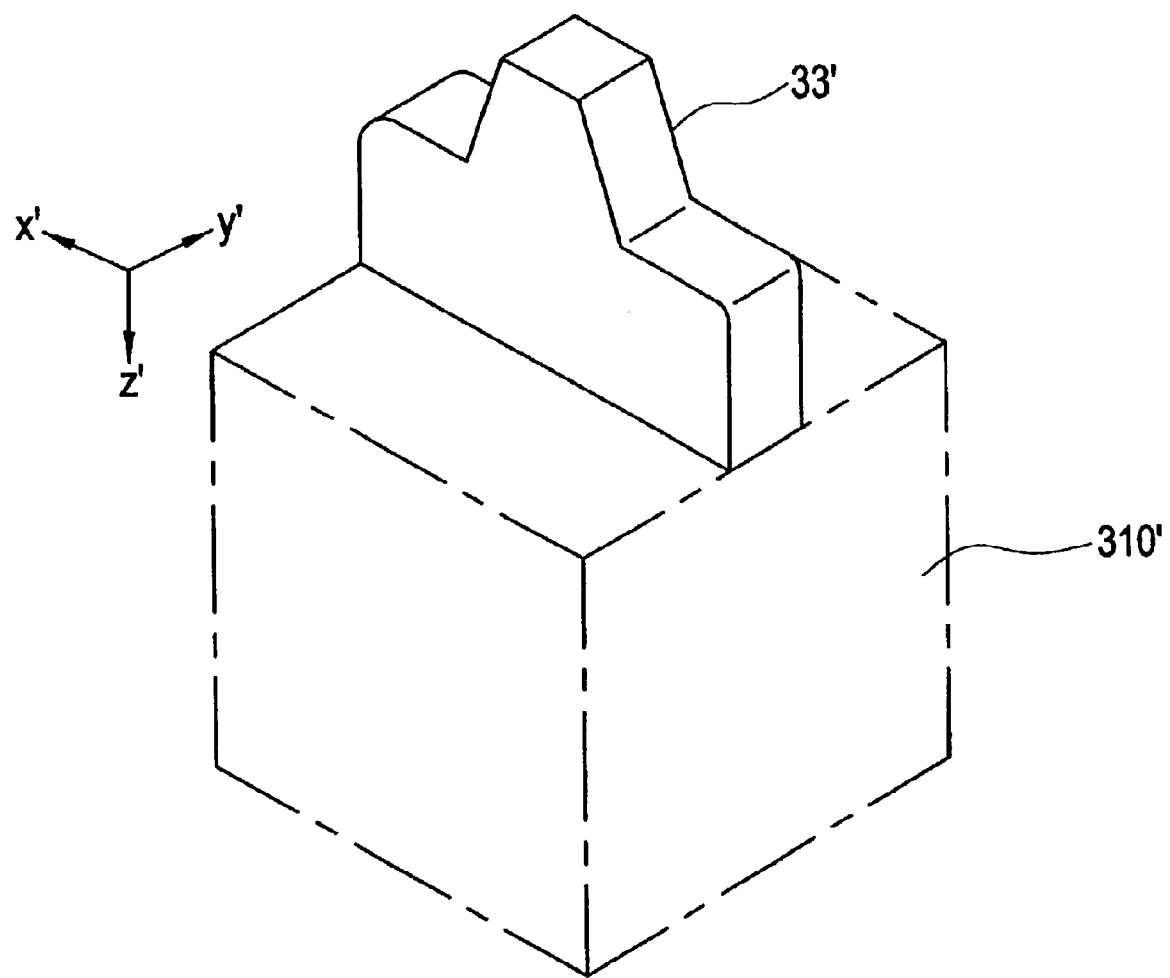
FIG. 16 shows a three-dimensional region.

The set reference position is defined as a reference position of a new three-dimensional region 310' as shown in FIG. 16. The three-dimensional region 310' corresponds to the three-dimensional region 310 shown in FIG. 12. Three mutually orthogonal directions in the three-dimensional region 310' are represented as x', y' and z'. They correspond to the three mutually orthogonal directions x, y and z in the three-dimensional region 310, respectively. If the size of the three-dimensional region 310 is 10 cm×10 cm×10 cm, for example, the size of the three-dimensional region 310' is 10 cm×10 cm×10 cm accordingly.

Next, at Step 910, direction specification is conducted. The direction means the imaging direction of an image produced by the post-processing. However, imaging is not actually conducted in that direction, and the imaging direction is a simulative direction. This direction will be sometimes referred to simply as the imaging direction hereinbelow.

The direction specification is achieved by the user using the ultrasonic probe 33'. The user operates the ultrasonic probe 33' as if he were conducting ultrasonic imaging. However, ultrasound is not transmitted or received. Moreover, the operation is directed not to the subject 7 but to the three-dimensional region 310'.

Figure 17:
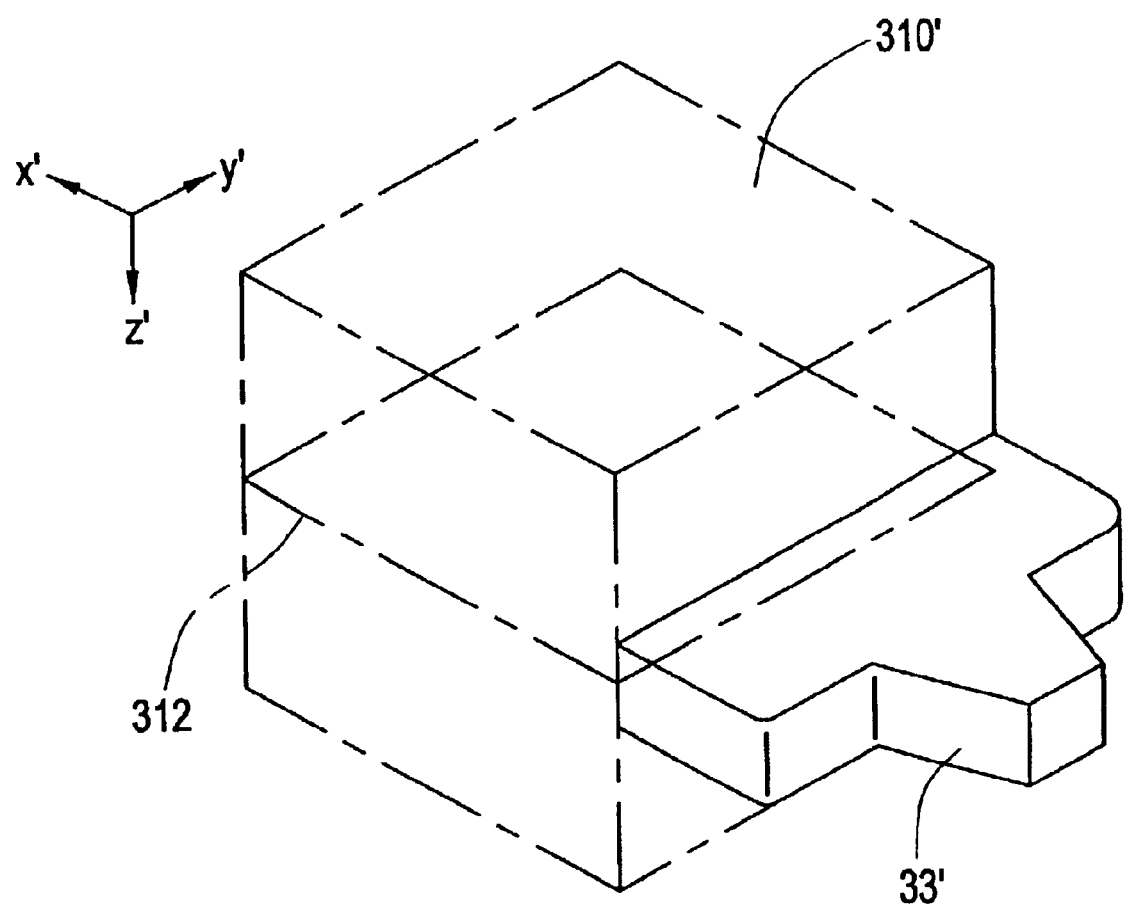
FIG. 17 shows a three-dimensional region.

Exemplary direction specification is shown in FIG. 17. As shown, the user brings the ultrasonic probe 33' into a horizontal attitude, and vertically applies it to a desired position in a y'-z' plane of the three-dimensional region 310'. At that time, the user imagines the three-dimensional region 310' in the air based on the reference position. Then, the user vertically applies the ultrasonic probe 33' to the desired position in the y'-z' plane of such an imaginary three-dimensional region 310'.

Since the reference position is set by the user himself, it is easy to imagine the three-dimensional region 310' in the air and it is easy to vertically apply the ultrasonic probe 33' to the desired position in the y'-z' plane of the three-dimensional region 310'. The x'-direction is thus specified as the imaging direction at the desired position in the three-dimensional region 310' in the z'-direction. The ultrasonic probe 33' is an embodiment of the specifying means of the present invention.

Next, at Step 912, image production is conducted. The image is produced by the image processing section 44 under control of the control section 48. Specifically, the control section 48 recognizes the specified imaging direction based on the three-dimensional location and attitude of the ultrasonic probe 33', and directs the image processing section 44 to produce an image corresponding to an image captured in the specified direction. The image processing section 44 produces the directed image from the three-dimensional image data.

The produced image is a tomographic image of a cross section 312, for example, as indicated by dot-dot-dash lines. The cross section 312 represents a main scan plane of the ultrasonic probe 33'. If the ultrasonic probe 33 is employed, the cross section 312 represents a θ scan plane at φ=0. The image to be produced is not limited to the tomographic image but may be a three-dimensional image. Which of the tomographic image or the three-dimensional image is to be produced can be selected by the user via the operating section 50. The image is displayed at Step 914. The displayed image is displayed as an image viewed in the z'-direction, for example.

The user observes such a displayed image. The image represents an image that is simulatively captured by the user actually operating the ultrasonic probe 33'. Therefore, the user can clearly perceive the imaging direction.

Thus, the user can have clear spatial perception on the displayed image. By observing the image with such spatial perception, a correct diagnosis is facilitated.

If the imaging direction is to be changed, the processing goes back to Step 910 in response to decision at Step 916. Then, similar simulative imaging is conducted in a new direction by the operations at Step 910 and later as described above, and an image by the simulative imaging is displayed.

The imaging direction can be freely specified by the user according to the application of the ultrasonic 33' with respect to the three-dimensional region 310'. Therefore, an image captured in any one of the x'-, y'- and z'-directions may be displayed.

The direction is not limited to the three directions, and it is possible to display an image captured in an arbitrarily selected oblique direction. This allows an image captured in a direction that is impossible in the actual imaging to be displayed. Since the imaging direction of an image is specified by his gesture, the user can observe any image with clear spatial perception.

Thereafter, similar simulative imaging is conducted on the three-dimensional region 310' by the ultrasonic probe 33' in various directions, and an image displayed each time is observed to carry out diagnosis.

By thus specifying an image direction by the ultrasonic probe, the direction specification is achieved by a gesture simulating ultrasonic imaging. This allows direction specification by the user without a feeling of incompatibility.

The specification of the imaging direction may be done using an appropriate dedicated direction indicator in place of the ultrasonic probe. The dedicated direction indicator has a shape simulating the ultrasonic probe 33', for example. By using such a direction indicator, discrimination from actual imaging is facilitated. In this case, the position sensor 37 is provided on the direction indicator.

The detection of the three-dimensional location and attitude of the ultrasonic probe or direction indicator may be conducted using light in place of magnetism. A schematic diagram in this case is shown in FIG. 18.

Figure 18:
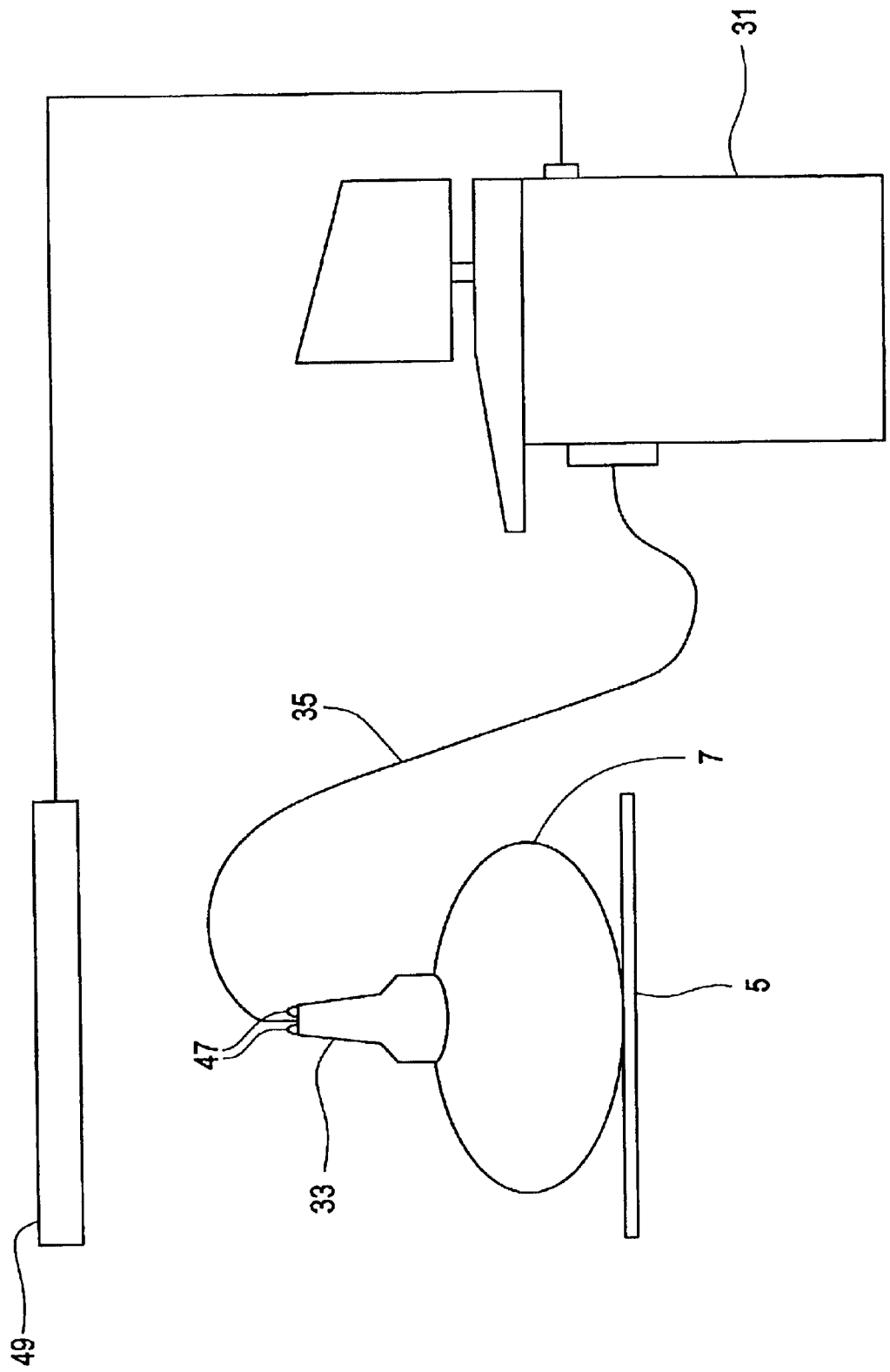
FIG. 18 schematically shows a configuration of the apparatus in accordance with one embodiment of the present invention.

As shown in FIG. 18, the ultrasonic probe 33 (or 33' or direction indicator; this applies to the following) is provided with a light emitter 47, and the emitted light is detected by a light spot detecting section 49 that is provided on the ceiling, for example. The light spot detecting section 49 has a plurality of light receiving portions capable of detecting the direction of light incidence, and determines the three-dimensional location of the light spot based on detected signals from the light receiving portions by the principal of triangulation.

The three-dimensional location of the light spot represents the three-dimensional location of the ultrasonic probe 33. By providing a plurality of the light emitters 47 in a predetermined geometrical relationship, the attitude of the ultrasonic probe 33 can be determined from the three-dimensional positional relationship of the light spots. Values thus determined are input to the imaging section main body 31.

Figure 19:
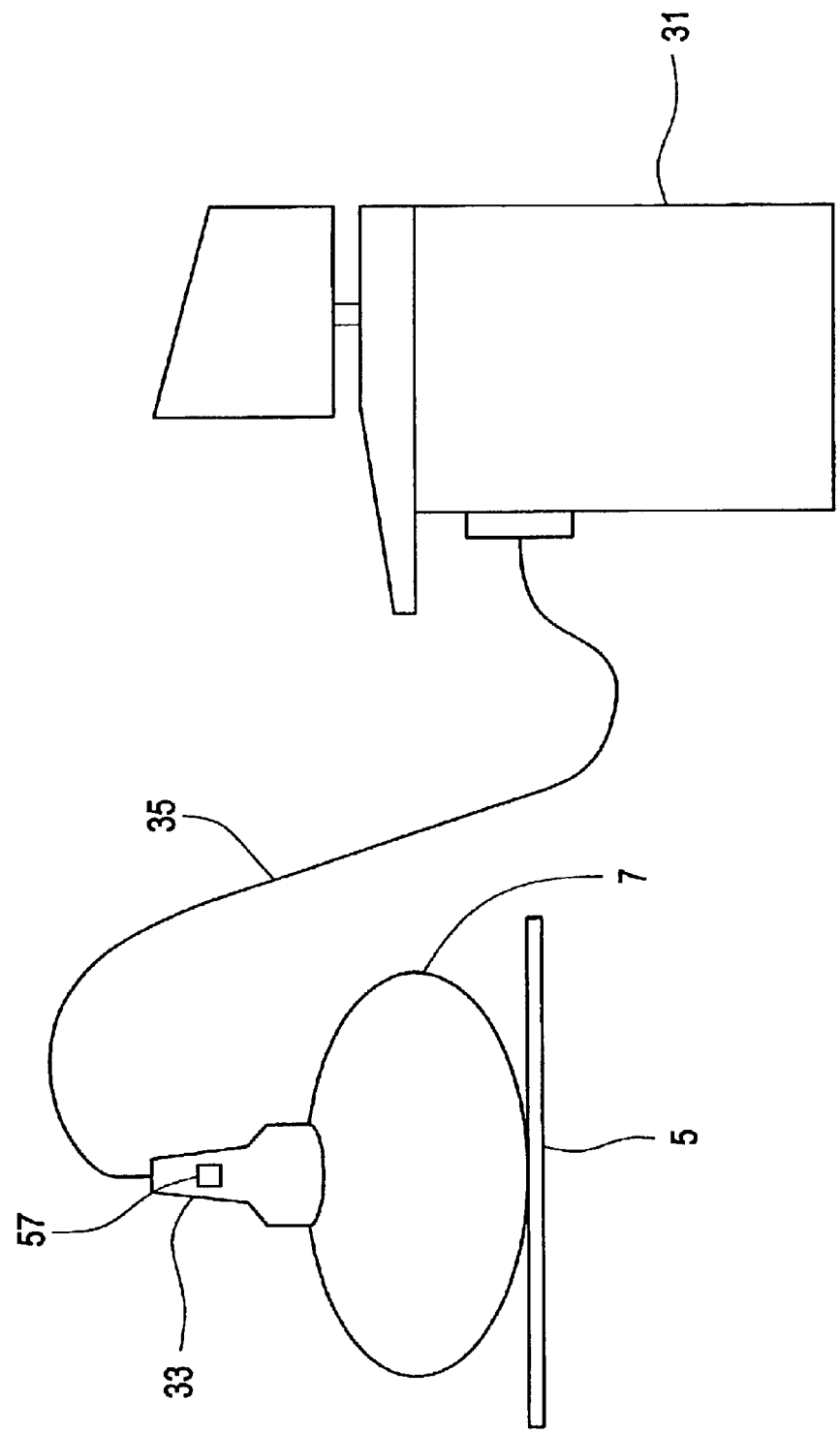
FIG. 19 schematically shows a configuration of the apparatus in accordance with one embodiment of the present invention.

The detection of the three-dimensional location and attitude of the ultrasonic probe or direction indicator may be conducted using acceleration. A schematic diagram in this case is shown in FIG. 19.

As shown, the ultrasonic probe 33 is provided with an acceleration sensor 57. The acceleration sensor 57 detects the acceleration in three directions. The detected signal is input to the imaging section main body 31 via the cable 35. In the imaging section main body 31, the three-dimensional location and attitude of the ultrasonic probe 33 are calculated by a predetermined calculation circuit such as the control section 48, based on the detected signal of acceleration. The location based on the acceleration is calculated by an integral calculation.

The detection of the three-dimensional location and attitude of the ultrasonic probe or direction indicator may be conducted by a mechanism for supporting the ultrasonic probe 33. A schematic diagram in this case is shown in FIG. 20.

As shown in FIG. 20, the ultrasonic probe 33 is supported by an articulated arm 67. Each joint in the articulated arm 67 has an angular sensor. Signals detected by the angular sensors are input to the imaging section main body 31. In the imaging section main body 31, the three-dimensional location and attitude of the ultrasonic probe 33 are calculated by a predetermined calculation circuit based on the detected signals of angles.

While the present invention has been described with reference to preferred embodiments, various changes or substitutions may be made on these embodiments by those ordinarily skilled in the art pertinent to the present invention without departing from the technical scope of the present invention. Therefore, the technical scope of the present invention encompasses not only those embodiments described above but all that fall within the scope of the appended claims.

What is claimed is:

1. An ultrasonic imaging apparatus comprising:
   data acquiring means for acquiring three-dimensional image data on a subject to be imaged based on ultrasound using an ultrasonic transceiver;
   specifying means for specifying a simulative imaging direction based on spatial information with respect to a hand instrument that is manually operated, wherein said specifying means specifies the simulative imaging direction when said specifying means is manipulated over an imaginary region; and
   image producing means for producing an image in said simulative imaging direction based on said three-dimensional image data.

2. The ultrasonic imaging apparatus of claim 1, wherein said specifying means has detecting means for detecting a three-dimensional location and attitude of said hand instrument.

3. The ultrasonic imaging apparatus of claim 2, wherein said detecting means uses magnetism to conduct the detection.

4. The ultrasonic imaging apparatus of claim 2, wherein said detecting means uses light to conduct the detection.

5. The ultrasonic imaging apparatus of claim 2, wherein said detecting means conducts the detection based on angles of joints in an articulated arm linked to said hand instrument.

6. The ultrasonic imaging apparatus of claim 2, wherein said detecting means includes a reference position for detecting a three-dimensional location and attitude of said hand instrument that can be set by a user of said hand instrument.

7. The ultrasonic imaging apparatus of claim 1, wherein said hand instrument has a magnetic sensor.

8. The ultrasonic imaging apparatus of claim 1, wherein said hand instrument has a light emitter.

9. The ultrasonic imaging apparatus of claim 1, wherein said detecting means uses acceleration to conduct the detection.

10. The ultrasonic imaging apparatus of claim 1, wherein said hand instrument has an acceleration sensor.

11. The ultrasonic imaging apparatus of claim 1, wherein said hand instrument is an ultrasonic transceiver.

12. The ultrasonic imaging apparatus of claim 1, wherein said hand instrument is a dedicated direction indicator.

13. The ultrasonic imaging apparatus of claim 1, wherein said data acquiring means has scanning means for electronically conducting a three-dimensional acoustic line scan.

14. The ultrasonic imaging apparatus of claim 1, wherein said data acquiring means has scanning means for conducting a three-dimensional acoustic line scan by a combination of an electronic scan and a mechanical scan.

15. The ultrasonic imaging apparatus of claim 1, wherein said image is a three-dimensional image.

16. The ultrasonic imaging apparatus of claim 1, wherein said image is a tomographic image.

* * * * *